United States Patent [19]
Sporck et al.

[11] Patent Number: 5,646,406
[45] Date of Patent: Jul. 8, 1997

[54] STROBOSCOPIC PHOTOMETER

[75] Inventors: A. Nicholas Sporck, Saratoga; Heng-Yang Lin, San Jose, both of Calif.

[73] Assignee: LSI Logic Corporation, Milpitas, Calif.

[21] Appl. No.: 652,999

[22] Filed: May 24, 1996

[51] Int. Cl.$^6$ .................................................. G01N 25/72
[52] U.S. Cl. ........................ 250/342; 250/330; 250/358.1
[58] Field of Search ................................. 250/342, 330, 250/341.4, 358.1

[56]  References Cited

U.S. PATENT DOCUMENTS 5,302,830  4/1994  Shivanandan ........................ 250/342
5,396,068  3/1995  Bethea ................................ 250/330

*Primary Examiner*—Carolyn E. Fields
*Attorney, Agent, or Firm*—Luedeka, Neely & Graham, P.C.

[57]  ABSTRACT

An apparatus for collecting photons emitted by hot spots in an integrated circuit. Means are provided for intermittently energizing the circuit. A photon receptor detects the photons emitted by the circuit, and produces a photon signal. A shutter, disposed between the circuit and the photon receptor, is opened by a controller when the circuit is not energized, and closed by the controller when the circuit is energized. By thus closing the shutter when the circuit is energized, the photon receptor is shielded from receiving the photons generated during the refresh cycle of the energized device, and is able to detect photons from a defect in the circuit over a period of time that is longer than the refresh rate of the circuit.

23 Claims, 1 Drawing Sheet

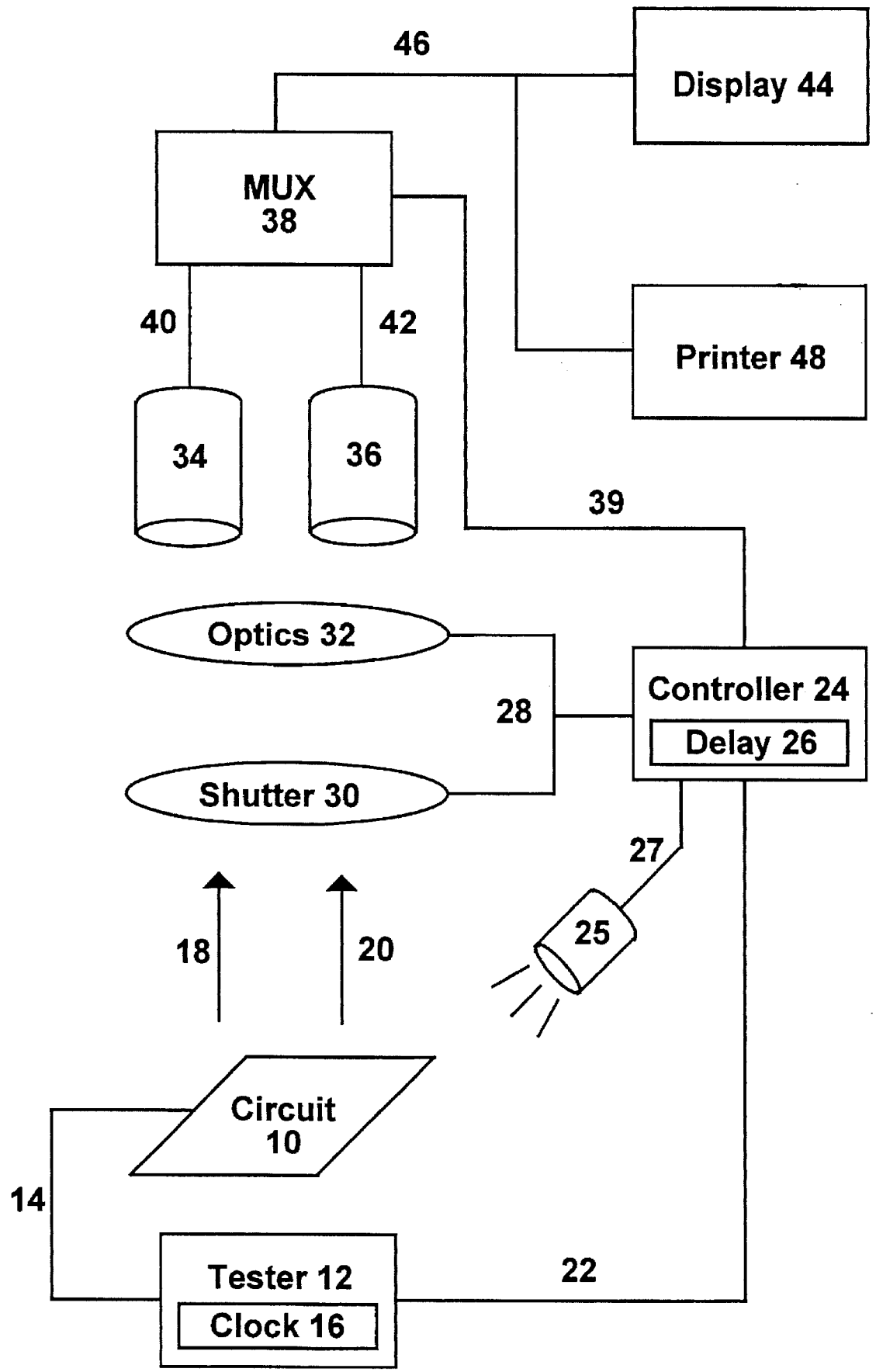

STROBOSCOPIC PHOTOMETER

FIELD OF THE INVENTION

This invention relates to the field of imaging. More particularly the invention relates to the field of background emission photometry of dynamic integrated circuits.

BACKGROUND OF THE INVENTION

In some types of integrated circuits, such as in semiconductor devices, current flowing through a defect in the circuit may cause electron-hole recombination. Current propagated in this manner creates photons which can be detected with a photon receptor. The receptor can resolve an image of the current path using the photons that are produced by recombination along the path. The method of imaging a circuit in this manner is generally termed background emission photometry.

The ability to trace the path taken by electrical current in a circuit is very useful. For example, in a circuit that is not operating correctly, such a representation of the current path may be useful in determining the location of the defect in the circuit. A short could be detected in this manner.

Depending on the amount of recombination occurring, it may take several minutes to collect enough photons for the receptor to make a distinguishable image. Thus, this type of imaging works well for static circuits which can hold an electrical charge for periods of time in excess of that required to resolve the image. An example of such a circuit would be a static random access memory device, or SRAM.

Dynamic devices, such as DRAM, or dynamic random access memory, cannot hold a charge for such a length of time. Therefore, dynamic devices are difficult to image with background emission photometry because relatively few photons are generated during the short time that the device holds a charge. The number of photons generated is typically insufficient for the photometer to resolve an image.

During normal operation, dynamic devices are typically refreshed on an intermittent basis. Unfortunately, when a device is refreshed in this manner, the current that flows through the circuit during the refresh cycle produces an enormous level of background photon emission. This high level of emission would obscure the photon emission from a defect, which typically carries less current that those portions of the circuit which are designed to carry current. Thus, background emission photometry has been of limited value in diagnosing dynamic integrated circuits.

What is needed, therefore, is a method and apparatus that overcomes the problem of high background emission levels attendant with intermittently energized circuits, and allows them to be analyzed with background emission photometry.

SUMMARY OF THE INVENTION

The above and other objects are met by an apparatus for collecting photons emitted by hot spots in an integrated circuit. A photon receptor detects the photons emitted by the circuit, and produces a photon signal. A shutter, disposed between the circuit and the photon receptor, is opened by a controller when the circuit is not energized, and closed by the controller when the circuit is energized. By thus closing the shutter when the circuit is energized, the photon receptor is shielded from receiving the photons generated during the refresh cycle of the energized device, and is able to detect photons from a defect in the circuit over a period of time that is longer than the refresh rate of the circuit.

In preferred embodiments a delay circuit is provided for keeping the shutter closed for a predetermined length of time after the circuit is not energized. This allows the background emission from the refresh cycle to subside before the photon receptor is again exposed to the photons from the circuit. A field of view covered by the photon receptor is preferably selectively optically adjusted. Further, a clock intermittently energizes the circuit at a predetermined rate, and provides a clock signal. The controller receives the clock signal, and closes and opens the shutter in response to the clock signal. In other preferred embodiments there is a camera which detects a reflected image of the circuit, and produces a camera signal, which is then combined into the photon signal by a multiplexor. A display and a printer receive the photon signal and present and print a representation of the emitted photons and reflected image.

In a method of collecting photons emitted by an integrated circuit according to the present invention, a clock signal having a predetermined rate as great as about one megahertz is provided. The integrated circuit is intermittently energized at the rate set by the clock signal, and photons emitted by the integrated circuit are detected with a charge-coupled device. A field of view covered by the photon receptor is selectively optically adjusted. A photon signal responsive to the detected photons is generated. The photons are blocked from detection when the clock signal indicates that the integrated circuit is energized, and the photons are blocked for an additional period as long as about one millisecond after the clock signal indicates that the integrated circuit is not energized.

A camera signal is produced with a charge-coupled device in response to a reflected image of the integrated circuit, and the camera signal is combined into the photon signal, which is received by a display. A representation of the emitted photons and reflected image is presented. The photon signal is also received with a printer, and a representation of the emitted photons and reflected image is printed.

BRIEF DESCRIPTION OF THE DRAWING

Further advantages of the invention will become apparent by reference to the detailed description of preferred embodiments when considered in conjunction with the FIGURE, which depicts a functional block diagram of an embodiment of a stroboscopic photometer according to the present invention.

DETAILED DESCRIPTION OF THE INVENTION

Referring now to the FIGURE, there is depicted a circuit 10 which is under test. The circuit 10 preferably comprises a semiconducting device, such as a type which propagates current by means of electron-hole recombination, and thus produces photons along the current paths. The purpose of the photometer depicted is to detect the location of, and other information about, defects that may be present in the circuit 10. Such defects are typically attendant with photon emission, or hot spots, that may be detected with a photometer.

The circuit 10 is also preferably a dynamic device. While the photometer described will function equally well to test a static device, there are particular aspects of a photometer according to the present invention, as described more fully below, that have particular application and relevance in the case of testing dynamic devices.

The circuit 10 is connected electrically to a tester 12 by means of a line 14. It will be appreciated that line 14, as with all other lines described herein, typically represents a plurality of electrical connections, shown here as a single line so as to not unduly encumber the FIGURE. The tester 12 provides power and control information to the circuit 10 via the line 14. Such control information may include, for example, signals indicating which current paths of the circuit 10 are to be activated. In this manner, a defective area of the circuit 10, which may have been electrically detected on another tester, may be further investigated using the photometer.

The tester 12 also preferably includes a clock 16, which provides a clock signal to the circuit 10. The circuit 10 is preferably intermittently energized at a rate corresponding to the clock signal provided by the clock 16. In a preferred embodiment the circuit 10 is intermittently energized at a rate as great as about one megahertz. At these frequencies the circuit 10 receives power at intervals as short as about one microsecond. While the circuit 10 may operate at a faster clock speed than this during normal operation, for the purposes of testing as described herein, the clock speed can be reduced.

The electron-hole recombination occurring in the circuit 10 tends to emit photons 18 from the current paths in the circuit 10. During those times when the circuit 10 is receiving power, there is a relatively high level of photons 18 being emitted, and during those times when the circuit 10 is not receiving power, there is a relatively reduced level of photons 18 being emitted.

If the circuit 10 was not intermittently energized in this manner, because it is preferably a dynamic device, a significant amount of the energy provided to the circuit 10 would dissipate after just a few clock cycles. When the energy stored in the circuit dissipated below a given amount, the logic states of the circuit 10 would tend to change. Thus, those portions of the circuit 10 which were selected for activation by the tester 12 would no longer be energized and produce photons. When this occurred it may no longer be possible to investigate the defects in the circuit 10 by means of photometry.

The clock signal produced by clock 16 is provided to a controller 24 on line 22. The controller 24 is connected to a shutter 30 by line 28. The controller 24 opens the shutter 30 when the circuit 10 is not being energized, and closes the shutter 30 when the circuit 10 is being energized. In the preferred embodiment, the controller 24 determines when the circuit 10 is or is not energized by means of the clock signal provided from the clock 16 on line 22.

Also in the preferred embodiment, the controller 24 has a delay circuit 26. The delay circuit 26 keeps the shutter 30 closed for a predetermined additional length of time as great as about one millisecond after the circuit 10 is not energized. This delay in opening the shutter 30 allows the latent photon emission from the current supplied during the refresh cycle of the circuit 10 to be blocked by the shutter 30 before it opens again. In a further preferred embodiment the delay circuit 26 closes the shutter 30 prior to refresh by a period of time as great as about one millisecond.

The photons 18 are detected by a photon receptor 34. The photon receptor 34 may be any device capable of detecting photons 18, such as a cascading electrode type photomultiplier vacuum tube, but in the preferred embodiment the photon receptor 34 is a charge coupled-device. Photons 18 are only detected by the photon receptor 34 during those times when the shutter 30, disposed between the circuit 10 and the photon receptor 34, is open. At times when the shutter 30 is closed, photons 18 are substantially inhibited from being detected by the photon receptor 34.

By closing the shutter 30 when the circuit 10 is energized, and preferably during the predetermined amount of time that any latent emission occurs as described above, the relatively large amount of photon 18 emission which occurs during this time is blocked from the detection of the photon receptor 34. Then when the shutter 30 opens when the circuit 10 is not being energized, the photon receptor 34 is able to continue detecting the relatively reduced amount of photons 18 which are produced by the circuit 10 when it is not energized.

In this manner the photon receptor 34 is able to detect photons 18 over a length of time that is greater than the refresh cycle of the circuit 10. The importance of this is that it may take this greater length of time to detect a sufficient amount of photons 18 to locate a defect within the circuit 10. If the shutter 34 remained open during the refresh cycle of the circuit 10, the relatively large amount of photon 18 emission during that time would tend to obscure the relatively reduced amount of photon 18 emission detected from a defect, thus making the defect more difficult, if not impossible, to detect.

The photon receptor 34 produces a photon signal from the detected photons 18, and sends the photon signal out on line 40. The photon signal may be delivered directly to a display 44 or a printer 38. However, in the preferred embodiment, the photon signal is first delivered to a multiplexor 38, before being sent to either the display 44 or the printer 48, or both, on line 46.

The controller 24 also preferably controls a light 25 via line 27, which selectively illuminates the circuit 10. The circuit 10 reflects light waves emitted by the light 25, which carry a reflected image 20 of the circuit 10. The light 25 is preferably turned off by the controller 24 at all times that the shutter 30 is open, so that the reflected image 20 does not confound the photon image generated by the photon receptor 34.

The reflected image 20 of the circuit 10 is preferably detected by a camera 36, which then produces a camera signal. The camera signal is delivered to the multiplexor 38 on line 42, and is combined into the photon signal, which combined signal may then be delivered to the display 44 or printer 48 as described above. In this manner the photon signal, which represents photons 18 that have been detected by the photon receptor 34, and the camera signal, which represents the reflected image 20 that has been detected by the camera 36, may be superimposed for review on the same display means, so that any hot spots that may be detected may be located visually as to physical position on the circuit 10.

However, in an alternate embodiment, the camera 36 and the photon receptor 34 are combined into a single receptor which provides the functions of each. In this embodiment the multiplexor 38, which could be provided in the form of a computer, could control the single receptor such that photons 18 are detected from the circuit 10 during those times when it is not energized, and the reflected image 20 is detected during those times when the circuit 10 is energized.

In this embodiment an effectual electronic shutter is supplied by the computerized multiplexor 38, making the physical shutter 30 unnecessary. Even in an embodiment where the camera 36 and the photon receptor 34 are separate elements, a computerized multiplexor 38 could turn the photon receptor 34 on and off as the circuit 10 is intermittently energized, again acting as an electronic shutter. In such embodiments, the multiplexor 38 is preferably in communication with the controller 24 via line 39.

In a further preferred embodiment, optical elements 32 are disposed between the circuit 10 and the photon receptor 34 and the camera 36. By use of the optical elements 32, the field of view on the circuit 10, detected by either the photon receptor 34 or the camera 36, may be selectively adjusted, such as enlarged or reduced, thus allowing an operator to either see more of the circuit 10, or magnify a selected area of the circuit 10 for a more detailed view and analysis. Adjusting the field of view, as used herein, includes adjusting the magnification of the circuit 10.

While the optical elements 32 as depicted in the FIGURE are disposed between the photon receptor 34 and the camera 36 and the shutter 30, it will be appreciated that other arrangements are possible, and may be preferable. For example, the optical elements 32 may be disposed between the shutter 30 and the circuit 10. Further, the camera 36 need not be on the opposite side of the shutter 30 from the circuit 10. Because the emission of photons 18 or the reflected image 20 during the energized cycle of the circuit 10 tends to have little or no degrading effect on the camera 36, it does not need to be shielded from the circuit 10 during the intermittent energizing cycles.

The entire apparatus described may be powered by a single power supply, which has not been depicted so as to keep the FIGURE simple, or each of the elements may be modular in configuration, with their own power supply. Similarly, the controller or tester 12 may provide a user interface through which an operator may input commands to the apparatus, or each element may again be modular and capable of receiving commands independently of the other elements through its own interface.

While specific embodiments of the invention have been described with particularity above, it will be appreciated that the invention is capable of numerous rearrangements and substitutions without departing from the scope of the invention.

What is claimed is:

1. An apparatus for collecting photons emitted by hot spots in a circuit, comprising:
   means for intermittently energizing the circuit,
   a photon receptor for detecting the photons emitted by the circuit, and producing a photon signal,
   a shutter disposed between the circuit and the photon receptor, and
   a controller for closing the shutter when the circuit is energized, and for opening the shutter when the circuit is not energized.

2. The apparatus of claim 1 further comprising a delay circuit for keeping the shutter closed for a predetermined length of time after the circuit is not energized.

3. The apparatus of claim 2 wherein the predetermined length of time is as great as about one millisecond.

4. The apparatus of claim 1 further comprising:
   a clock for intermittently energizing the circuit at a predetermined rate as great as about one megahertz, and for providing a clock signal, and
   the controller for receiving the clock signal, and for closing and opening the shutter in response to the clock signal.

5. The apparatus of claim 4 further comprising a delay circuit for keeping the shutter closed for as long as about one millisecond after the clock signal indicates that the circuit is not energized.

6. The apparatus of claim 1 wherein the photon receptor further comprises a charge-coupled device.

7. The apparatus of claim 1 further comprising a display for receiving the photon signal and presenting a representation of the emitted photons.

8. The apparatus of claim 1 further comprising a printer for receiving the photon signal and printing a representation of the emitted photons.

9. The apparatus of claim 1 further comprising:
   a camera for detecting a reflected image of the circuit and producing a camera signal, and
   a multiplexor for combining the camera signal into the photon signal.

10. The apparatus of claim 9 wherein the camera further comprises a charge-coupled device.

11. The apparatus of claim 1 further comprising optical elements disposed between the circuit and the photon receptor for selectively optically adjusting a field of view covered by the photon receptor.

12. An apparatus for collecting photons emitted by an integrated circuit, comprising:
   a clock for intermittently energizing the integrated circuit at a rate as great as about one megahertz, and for providing a clock signal,
   a photon receptor for detecting the photons emitted by the integrated circuit with a charge-coupled device, and producing a photon signal,
   optical elements disposed between the integrated circuit and the photon receptor for selectively optically adjusting a field of view covered by the photon receptor,
   a shutter disposed between the integrated circuit and the photon receptor,
   a controller for receiving the clock signal, for closing the shutter when the clock signal indicates that the integrated circuit is energized, and for opening the shutter when the clock signal indicates that the integrated circuit is not energized,
   a delay circuit for keeping the shutter closed for as long as about one millisecond after the clock signal indicates that the integrated circuit is not energized,
   a camera for detecting a reflected image of the integrated circuit with a charge-coupled device, and producing a camera signal,
   a multiplexor for combining the camera signal into the photon signal,
   a display for receiving the photon signal and presenting a representation of the emitted photons and reflected image, and
   a printer for receiving the photon signal and printing a representation of the emitted photons and reflected image.

13. A method of collecting photons emitted by an integrated circuit, comprising:
   providing a clock signal having a predetermined rate,
   intermittently energizing the circuit at the predetermined rate set by the clock signal,
   detecting the photons emitted by the circuit,
   generating a photon signal responsive to the detected photons, and
   blocking the photons from being detected when the clock signal indicates that the circuit is energized.

14. The method of claim 13 further comprising blocking the photons for an additional predetermined length of time after the clock signal indicates that the circuit is not energized.

15. The method of claim 14 wherein the predetermined length of time is as great as about one millisecond.

16. The method of claim 13 wherein the predetermined rate is as great as about one megahertz.

17. The method of claim 13 wherein the step of detecting the photons further comprises detecting the photons with a charge-coupled device.

18. The method of claim 13 further comprising:

receiving the photon signal with a display, and presenting a representation of the emitted photons.

19. The method of claim 13 further comprising:

receiving the photon signal with a printer, and printing a representation of the emitted photons.

20. The method of claim 13 further comprising:

producing a camera signal in response to a reflected image of the circuit, and combining the camera signal into the photon signal.

21. The method of claim 20 wherein the step of producing the camera signal further comprises producing the camera signal with a charge-coupled device.

22. The method of claim 13 further comprising selectively optically adjusting a field of view covered by the photon receptor.

23. A method of collecting photons emitted by an integrated circuit, comprising:

providing a clock signal having a rate as great as about one megahertz, intermittently energizing the integrated circuit at the rate set by the clock signal, detecting the photons emitted by the integrated circuit with a charge-coupled device, selectively optically adjusting a field of view covered by the photon receptor, generating a photon signal responsive to the detected photons, blocking the photons from being detected when the clock signal indicates that the integrated circuit is energized, blocking the photons for and additional period of as long as about one millisecond after the clock signal indicates that the integrated circuit is not energized, producing a camera signal in response to a reflected image of the integrated circuit with a charge-coupled device, combining the camera signal into the photon signal, receiving the photon signal with a display, presenting a representation of the emitted photons and reflected image, receiving the photon signal with a printer, and printing a representation of the emitted photons and reflected image.

\* \* \* \* \*